United States Patent
Davison et al.

(10) Patent No.: US 6,187,000 B1
(45) Date of Patent: *Feb. 13, 2001

(54) CANNULA FOR RECEIVING SURGICAL INSTRUMENTS

(75) Inventors: Thomas W. Davison, North Attelboro; Timothy E. Taylor, Attelboro; Adam Sher, North Dartmouth, all of MA (US)

(73) Assignee: Endius Incorporated, Plainville, MA (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/137,335

(22) Filed: Aug. 20, 1998

(51) Int. Cl.[7] .................................................. A61B 17/00
(52) U.S. Cl. ................................. 606/1; 606/198; 604/105
(58) Field of Search ........................... 606/1, 191, 198, 606/184, 185; 604/104, 105

(56) References Cited

U.S. PATENT DOCUMENTS

| 3,044,461 | 7/1962 | Murdock . |
| 4,899,729 | 2/1990 | Gill et al. . |
| 5,163,949 | * 11/1992 | Bonutti ................................ 606/198 |
| 5,197,971 | * 3/1993 | Bonutti ................................ 606/198 |
| 5,354,302 | 10/1994 | Ko . |
| 5,707,359 | 1/1998 | Bufalini . |
| 5,902,231 | 5/1999 | Foley et al. . |

FOREIGN PATENT DOCUMENTS 807415   11/1997   (EP) .

OTHER PUBLICATIONS

Med—MicroEndoscopic Discectomy System, brochure by Sofamore Danek.

* cited by examiner

Primary Examiner—Michael Buiz
Assistant Examiner—William Lewis
(74) Attorney, Agent, or Firm—Tarolli, Sundheim, Covell, Tummino & Szabo L.L.P.

(57) ABSTRACT

A cannula (10) receives surgical instruments (120) for performing a surgical procedure on a body (130). The cannula (10) comprises a tube structure (12) defining a passage (16) through which the surgical instruments (120) are inserted into the body (130). The tube structure (12) has a proximal end (20) and a distal end (62). The tube structure (12) includes an expandable portion (40) for enabling an increase in the cross-sectional area of the passage (16) at the distal end (62). The expandable portion (40) of the tube structure (12), when expanded, has a conical configuration.

22 Claims, 2 Drawing Sheets

CANNULA FOR RECEIVING SURGICAL INSTRUMENTS

TECHNICAL FIELD

The present invention is directed to a cannula for receiving surgical instruments for performing a surgical procedure on a body.

BACKGROUND OF THE INVENTION

Endoscopic surgical techniques allow a surgical procedure to be performed on a patient's body through a relatively small incision in the body and with a limited amount of body tissue disruption. Endoscopic surgery typically utilizes a tubular structure known as a cannula which is inserted into a small incision in the body. The cannula holds the incision open and serves as a conduit extending between the exterior of the body and the local area inside the body where the surgery is to be performed.

Due to the relatively small size of the passage into the body which is defined by the cannula, certain surgical procedures, such as posterior disectomies and procedures using steerable surgical instruments, have been difficult to perform using endoscopic techniques.

SUMMARY OF THE INVENTION

The present invention is a cannula for receiving surgical instruments for performing a surgical procedure on a body. The cannula comprises a tube structure defining a passage through which the surgical instruments are inserted into the body. The tube structure has a proximal end and a distal end. The tube structure includes an expandable portion for enabling an increase in the cross-sectional area of the passage at least at the distal end.

The expandable portion of the tube structure, when expanded, has a conical configuration. The expandable portion of the tube structure includes an arcuate slot and a guide pin disposed in the arcuate slot. The guide pin is movable from a terminal end of the slot to a second terminal end of the slot to enable the cross-sectional area of the passage at the distal end to increase.

The tube structure includes first and second tubular portions attached to one another. The second tubular portion comprises the expandable portion. The first tubular portion comprises a length of stainless steel tubing and the second tubular portion comprises an arcuate segment of stainless steel sheet stock rolled into a tubular shape.

BRIEF DESCRIPTION OF THE DRAWINGS

The foregoing and other features of the present invention will becomes apparent to one skilled in the art to which the present invention relates upon consideration of the following description of the invention with reference to the accompanying drawings, wherein.

DESCRIPTION OF PREFERRED EMBODIMENTS

The present invention is directed to a cannula for receiving surgical instruments for performing a surgical procedure on the body of a patient. The present invention is applicable to a variety of surgical procedures in which endoscopic surgical techniques are used.

Figure 1:
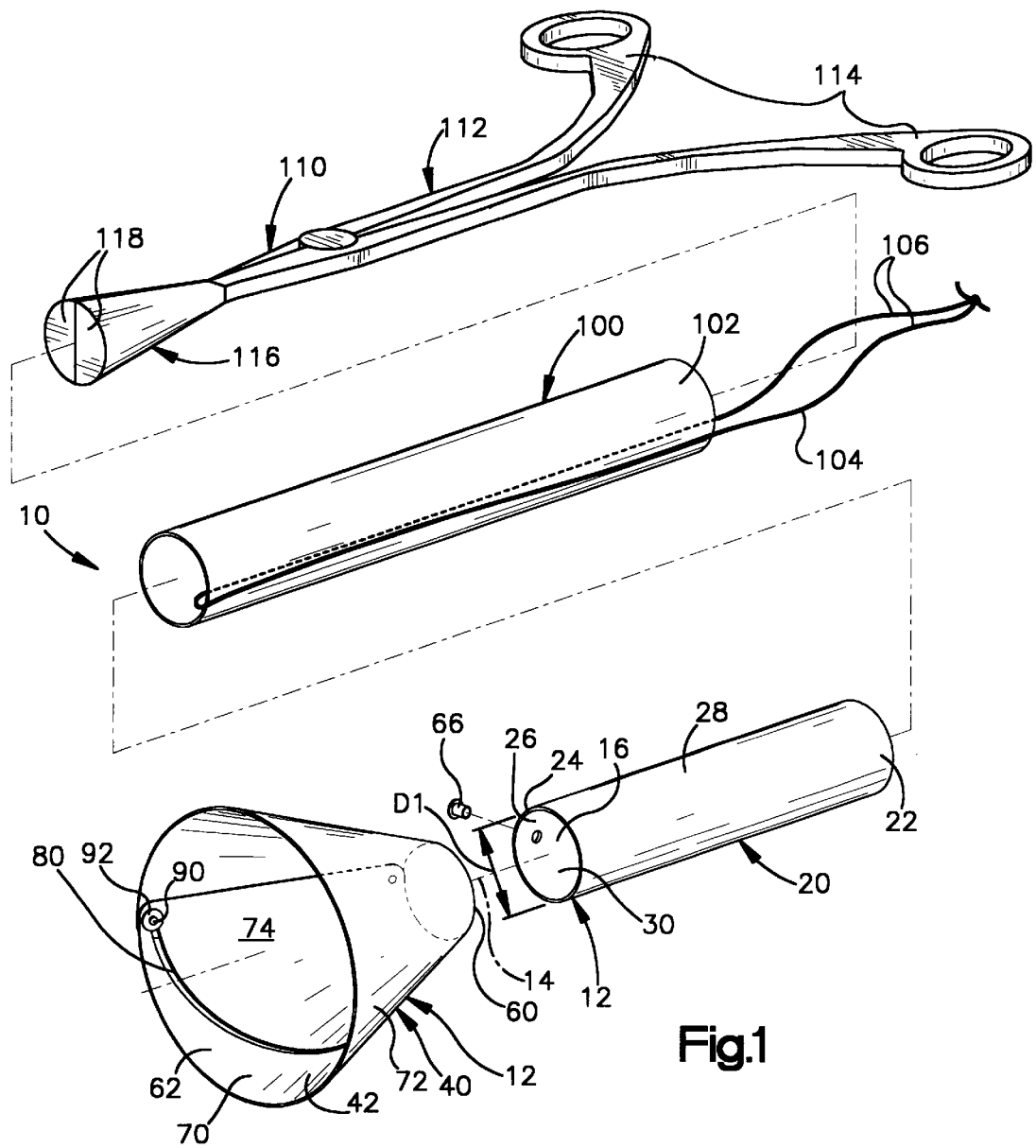
FIG. 1 is an exploded perspective view of a surgical cannula constructed in accordance with the present invention, the cannula being shown in an expanded condition.

FIG. 1 illustrates a cannula 10 constructed according to the present invention. The cannula 10 is a tubular structure 12 centered on an axis 14. The tubular structure 12 defines a passage 16 through the cannula 10. Surgical instruments are inserted into the body during endoscopic surgery through the passage 16.

The tubular structure 12 comprises a first tubular portion 20 and a second tubular portion 40 attached to the first tubular portion. The first tubular portion 20 is preferably made of a length of stainless steel tubing, but could alternatively be made of another suitable material. The first tubular portion 20 has a proximal end 22 and a distal end 24. Parallel cylindrical inner and outer surfaces 26 and 28, respectively, extend between the ends 22, 24 of the first tubular portion 20. The inner surface 26 defines a first passage portion 30 of the passage 16 through the cannula 10. The first passage portion 30 has a diameter D1 which is preferably in the range from 10 mm to 20 mm.

The second tubular portion 40 of the tubular structure 12 is attached to the distal end 24 of the first tubular portion 20. The second tubular portion is preferably made from stainless steel, but could alternatively be made from another suitable material.

Figure 4:
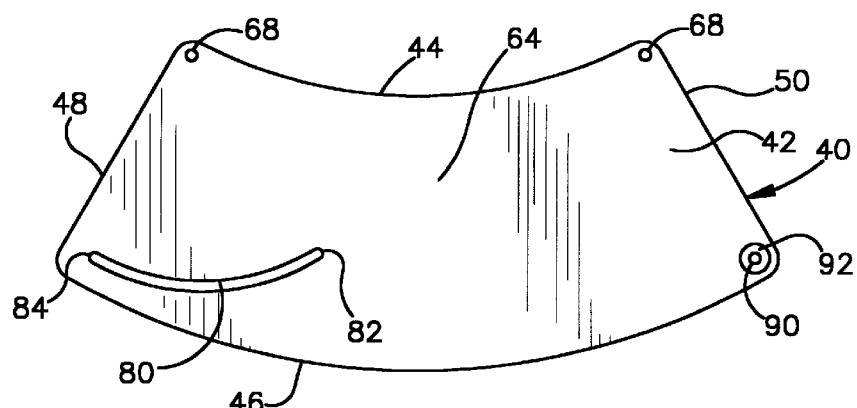
FIG. 4 is a roll out view of a part of the cannula of FIG. 1.

As best seen in the rollout view of FIG. 4, the second tubular portion 40 comprises an arcuate segment 42 of sheet stock. The arcuate segment 42 includes first and second arcuate edges 44 and 46, respectively, and first and second planar edges 48 and 50, respectively. The first and second planar edges 48 and 50 are rolled in an overlapping manner to form the tubular configuration of the second tubular portion 40.

When the second tubular portion 40 has been rolled into its tubular configuration, the first and second arcuate edges 44 and 46 define oppositely disposed first and second ends 60 and 62 (FIGS. 1 and 2), respectively, of the second tubular portion. The first and second ends 60 and 62 are connected by a central portion 64. The first end 60 of the second tubular portion 40 is attached to the distal end 24 of the first tubular portion 20 by a single fastener, such as a rivet 66. The rivet 66 extends through two aligned apertures 68 (FIG. 4) at the first end 60 of the second tubular portion 40. The first end 60 of the second tubular portion 40 is pivotable about the rivet 66.

The second tubular portion 40 includes parallel inner and outer surfaces 70 and 72 (FIGS. 1 and 2), respectively, extending between the first and second ends 60 and 62. The inner surface 70 defines a second passage portion 74 of the passage 16 through the cannula 10 which extends as a continuation of the first passage portion 30 in the first tubular portion 20.

An arcuate slot 80 is formed in the second tubular portion 40 and extends between the inner and outer surfaces 70 and 72 of the second tubular portion. The arcuate slot 80 extends along a curvilinear path in the central portion 64 of the second tubular portion 40 toward the second end 60 of the second tubular portion. The arcuate slot 80 has a first terminal end 82 located in the central portion 64 of the second tubular portion 40. A second terminal end 84 of the arcuate slot 80 is located adjacent the intersection of the second arcuate edge 46 and the first planar edge 48 of the arcuate segment 42.

A guide pin 90 is attached to the inner surface 70 of the second tubular portion 40 adjacent the intersection of the second arcuate edge 46 and the second planar edge 50. In the tubular configuration of the second tubular portion 40, the guide pin 90 is located in the arcuate slot 80 and is movable along the curvilinear path of the arcuate slot. A washer 92 is secured an inner end of the guide pin 90 to retain the guide pin in the arcuate slot 80.

Figure 2:
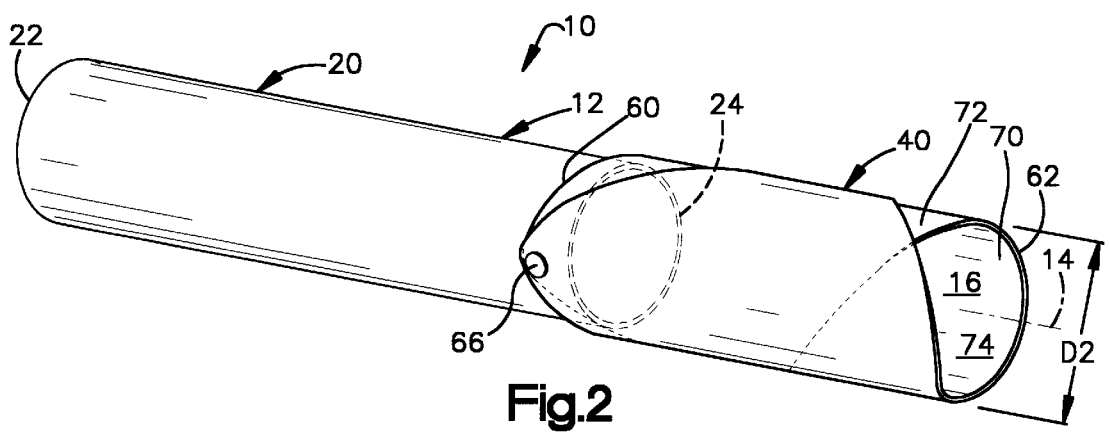
FIG. 2 is a perspective view of the cannula of FIG. 1 with parts removed for clarity, the cannula being shown in a contracted condition.
Figure 3:
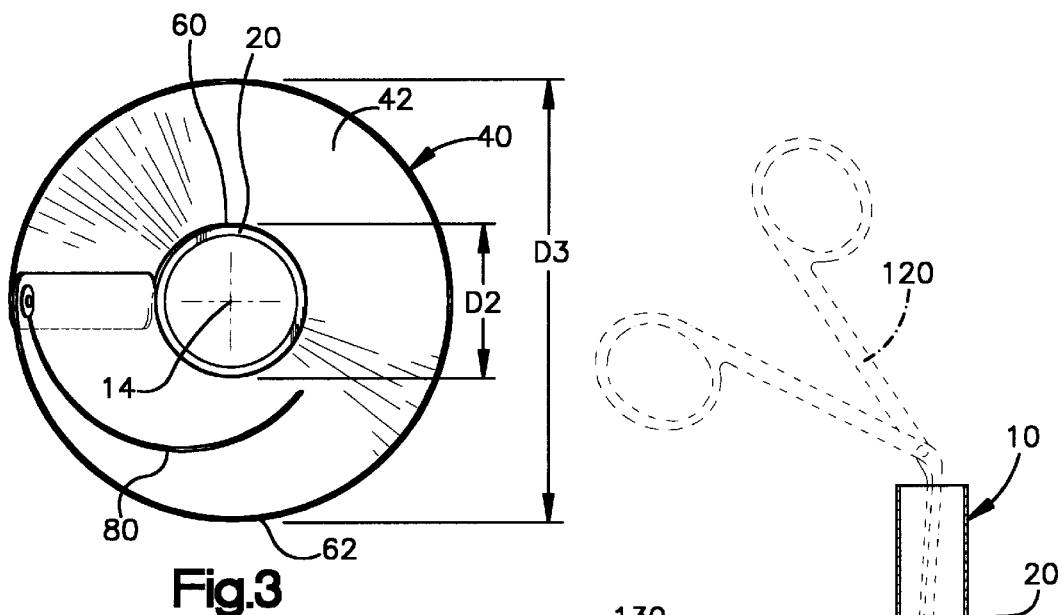
FIG. 3 is a schematic end view showing the cannula of FIG. 1 in the expanded position.

The second tubular portion 40 of the tubular structure 12 is expandable from a contracted condition shown in FIG. 2 to an expanded condition shown in FIG. 1. In the contracted condition, the guide pin 90 is located in the first terminal end 82 of the arcuate slot 80 in the second tubular portion 40 and the second passage portion 74 defined by the second tubular portion is cylindrical in shape. The second passage 74 has a generally constant diameter D2 (FIGS. 2 and 3) which is approximately equal to the diameter D1 of the first tubular portion 20. Thus, the cross-sectional area of the second passage portion 74 at the second end 62 of the second tubular portion 40, which is function of the diameter D2, is approximately the same as the cross-sectional area at the first end 60 of the second tubular portion and is approximately the same as the cross-sectional area of the first passage portion 30 in the first tubular portion 20.

In the expanded condition, the guide pin 90 is located in the second terminal end 84 of the arcuate slot 80 in the second tubular portion 40 and the second tubular portion has a conical configuration. At the second end 62 of the second tubular portion 40, the second passage portion 74 has a diameter D3 (FIG. 3) which is larger then the diameter D2 of the second passage portion at the first end 60. Preferably, the diameter D3 of the second passage portion 74 at the second end 62 of the second tubular portion is 40% to 80% greater than the diameter D1 of the second passage portion at the first end 60. Thus, in the expanded condition, the cross-sectional area of the second passage portion 74 at the second end 62 of the second tubular portion 40, which is function of the diameter D3, is 40% to 80% greater than the cross-sectional area of the second passage portion at the first end 60 of the second tubular portion.

The cannula 10 includes an outer layer 100 (FIG. 1) for maintaining the second tubular portion 40 of the cannula in the contracted condition. It is contemplated that other suitable means for maintaining the second tubular portion 40 in the contracted condition could be employed. In accordance with a preferred embodiment of the present invention, the outer layer 100 comprises a section of plastic tubing 102 which is heat shrunk over both the first and second tubular portions 20 and 40 to hold the second tubular portion in the contracted condition.

In addition, a loop of nylon string 104 for tearing the heat shrunk tubing 102 is wrapped around the heat shrunk tubing so that it extends both underneath and on top of the tubing. An outer end 106 of the string 104 extends beyond the tubing 102.

The cannula 10 further includes an actuatable device 110 for expanding the second tubular portion 40 from the contracted condition to the expanded condition. In accordance with a preferred embodiment of the present invention, the actuatable device 110 comprises a manually operated expansion tool 112. The expansion tool 112 resembles a common pair of scissors and has a pair of legs 114 pivotally connected to one another. The expansion tool 112 includes a frustoconical end section 116 formed by a pair of frustoconical halves 118. Each of the frustoconical halves 118 extends from a respective one of the legs 114 of the expansion tool 112. It is contemplated that other suitable means for expanding the second tubular portion 40 toward the expanded condition could be employed, such as an inflatable balloon (not shown).

During an endoscopic surgical procedure, the cannula 10 is inserted into the body of a patient in the contracted condition. The outer end 106 of the string 104 is then manually pulled on by the surgeon. Pulling on the string 104 tears the heat shrunk tubing 102 which is then removed from the cannula 10 by the surgeon. With the heat shrink tubing 102 removed, the second tubular portion 40 of the cannula 10 is thereby released for expansion toward the expanded condition.

Figure 5:
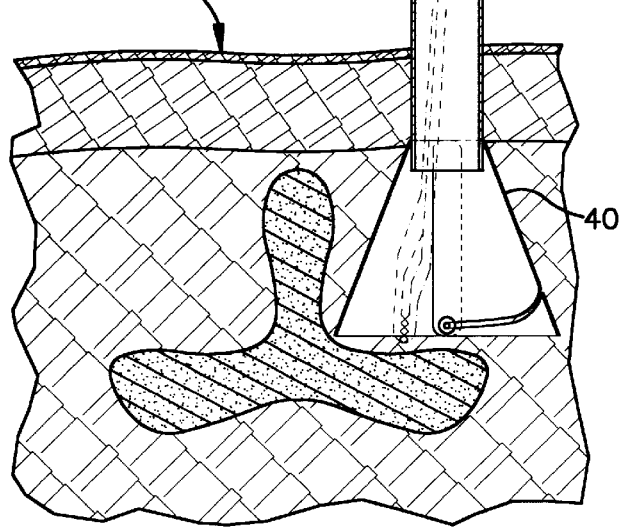
FIG. 5 is a schematic sectional view of the cannula of FIG. 1 during a surgical procedure.

Next, the expansion tool 112 is inserted into the passage 16 in the cannula 10 until the frustoconical end section 114 is located at the second end 62 of the second tubular portion 40. The legs 114 of the expansion tool 112 are manually separated, causing the frustoconical halves 118 to separate also. As the halves 118 separate, a radially outward directed force is exerted on the inner surface 70 of the second tubular portion 40 by the halves 118, causing the second tubular portion to expand toward the expanded condition. Under the force of the expanding expansion tool 112, the guide pin 90 slides from the first terminal end 82 of the arcuate slot 80 to the second terminal end 84 of the arcuate slot to permit the expansion of the second tubular portion 40. The expansion tool 112 can be rotated about the axis 14 to ensure that the second tubular portion 40 of the cannula 10 is completely expanded to the expanded condition. The expansion tool 112 is then collapsed and removed so that one or more surgical instruments (indicated schematically at 120 in FIG. 5) can be received through the cannula 10 and inserted into a patient's body 130.

The expandable second tubular portion 40 of the cannula 10 provides a significantly larger working area for the surgeon inside the body 130 within the confines of the cannula. As a result, the simultaneous use of a number of endoscopic surgical instruments, including but not limited to steerable instruments, shavers, dissectors, scissors, forceps, retractors, dilators, and video cameras, is made possible by the expandable cannula 10.

It is contemplated that the cannula 10 described herein could be the centerpiece of a endoscopic surgical kit which would include an assortment of surgical instruments designed and/or selected for use with the cannula.

From the above description of the invention, those skilled in the art will perceive improvements, changes and modifications. Such improvements, changes and modifications within the skill of the art are intended to be covered by the appended claims.

Having described the invention, we claim:

1. A cannula for receiving surgical instruments for performing a surgical procedure on a body, said cannula comprising:
   a tube structure having an outer surface for engaging the body and an inner surface, said inner surface defining a passage extending through the tube structure and through which the surgical instruments are inserted into the body, said tube structure having a proximal end and a distal end, said passage having a first cross-sectional area between said proximal end and said distal end, said tube structure including an expandable portion for enabling an increase in the cross-sectional area of said passage at said distal end of said tube structure to a second cross-sectional area which is greater than said first cross-sectional area.

2. The cannula of claim 1 wherein said expandable portion of said tube structure, when expanded, has a conical configuration.

3. The cannula of claim 1 wherein said tube structure is made of metal.

4. The cannula of claim 1 wherein said expandable portion is expandable from a contracted condition to an expanded condition to increase the cross-sectional area of said passage at said distal end of said tube structure.

5. The cannula of claim 4 further comprising means for maintaining said expandable portion in said contracted condition, said means being manually actuatable to release said expandable portion for expansion from said contracted condition.

6. The cannula of claim 4 further comprising means for expanding said expandable portion from said contracted condition to said expanded condition, said means being insertable into said passage and actuatable to apply a radially outwardly directed force to expand said expandable portion.

7. The cannula of claim 1 wherein said tube structure includes first and second tubular portions attached to one another, said second tubular portion comprising said expandable portion.

8. A cannula for receiving surgical instruments, said cannula comprising:
    a first tubular portion having a first outer surface for engaging the body and a first inner surface defining a first passage for receiving the surgical instruments, said first passage having a first diameter, said first tubular portion having a proximal end and a distal end; and
    a second tubular portion attached to said distal end of said first tubular portion, said second tubular portion having a second outer surface for engaging the body and a second inner surface defining a second passage for receiving the surgical instruments, said second passage being a continuation of said first passage,
    said second tubular portion being diametrically expandable to enable enlargement of said second passage to a size which is greater than said first diameter of said first passage.

9. The cannula of claim 8 wherein said second tubular portion has oppositely disposed first and second ends, said first end being attached to said distal end of said first tubular portion.

10. The cannula of claim 9 wherein said second passage at said second end of said second tubular portion, when said second tubular portion is expanded, has a second diameter which is greater than said first diameter of said first passage in said first tubular portion.

11. The cannula of claim 8 wherein said second passage, when said second tubular portion is expanded, has a conical configuration.

12. The cannula of claim 8 wherein said first and second tubular portions are made of metal.

13. The cannula of claim 12 wherein said first tubular portion comprises a length of stainless steel tubing.

14. The cannula of claim 8 wherein said second tubular portion is expandable from a contracted condition to an expanded condition to enable enlargement of said second passage.

15. The cannula of claim 14 further comprising means for maintaining said second tubular portion in said contracted condition, said means being manually actuatable to release said second tubular portion for expansion from said contracted condition.

16. The cannula of claim 14 further comprising means for expanding said second tubular portion from said contracted condition to said expanded condition, said means being insertable into said first passage and actuatable to apply a radially outwardly directed force to expand said second passage.

17. A cannula for receiving surgical instruments for performing a surgical procedure on a body, said cannula comprising:
    a tube structure defining a passage through which the surgical instruments are inserted into the body, said tube structure having a proximal end and a distal end,
    said tube structure including an expandable portion for enabling an increase in the cross-sectional area of said passage at said distal end;
    said expandable portion of said tube structure having an arcuate slot and a guide pin disposed in said arcuate slot, said guide pin being movable from a first terminal end of said slot to a second terminal end of said slot to enable the cross-sectional area of said passage at said distal end to increase.

18. A cannula for receiving surgical instruments for performing a surgical procedure on a body, said cannula comprising:
    a tube structure defining a passage through which the surgical instruments are inserted into the body, said tube structure having a proximal end and a distal end,
    said tube structure including an expandable portion for enabling an increase in the cross-sectional area of said passage at said distal end;
    said tube structure including first and second tubular portions attached to one another, said second tubular portion comprising said expandable portion;
    said first tubular portion comprising a length of stainless steel tubing and said second tubular portion comprising an arcuate segment of stainless steel sheet stock rolled into a tubular shape.

19. A cannula for receiving surgical instruments, said cannula comprising:
    a first tubular portion defining a first passage for receiving the surgical instruments, said first passage having a first diameter, said first tubular portion having a proximal end and a distal end; and
    a second tubular portion attached to said distal end of said first tubular portion and defining a second passage for receiving the surgical instruments, said second passage being a continuation of said first passage,
    said second tubular portion being diametrically expandable to enable enlargement of said second passage to a size which is greater than said first diameter of said first passage;
    said second tubular portion having oppositely disposed first and second ends, said first end being attached to said distal end of said first tubular portion;
    said second passage at said second end of said second tubular portion, when said second tubular portion is expanded, having a second diameter which is greater than said first diameter of said first passage in said first tubular portion;
    said second diameter of said second passage at said second end of said second tubular portion, when said second tubular portion is expanded, being 40% to 80% larger than said first diameter of said first passage.

20. A cannula for receiving surgical instruments, said cannula comprising:

a first tubular portion defining a first passage for receiving the surgical instruments, said first passage having a first diameter, said first tubular portion having a proximal end and a distal end; and a second tubular portion attached to said distal end of said first tubular portion and defining a second passage for receiving the surgical instruments, said second passage being a continuation of said first passage, said second tubular portion being diametrically expandable to enable enlargement of said second passage to a size which is greater than said first diameter of said first passage;

said second tubular portion having an arcuate slot and a guide pin disposed in said arcuate slot, said guide pin being movable from a first terminal end of said arcuate slot to a second terminal end of said arcuate slot to enable said second tubular portion to expand diametrically.

21. The cannula of claim 20 wherein said second tubular portion has first and second ends connected by a central portion, said first end being attached to said distal end of said first tubular portion, said arcuate slot extending circumferentially from said central portion toward said second end.

22. A cannula for receiving surgical instruments, said cannula comprising:

a first tubular portion defining a first passage for receiving the surgical instruments, said first passage having a first diameter, said first tubular portion having a proximal end and a distal end; and a second tubular portion attached to said distal end of said first tubular portion and defining a second passage for receiving the surgical instruments, said second passage being a continuation of said first passage, said second tubular portion being diametrically expandable to enable enlargement of said second passage to a size which is greater than said first diameter of said first passage;

said first and second tubular portions being made of metal;

said second tubular portion comprising an arcuate segment of stainless steel sheet stock.

* * * * *